(12) United States Patent
Naito et al.

(10) Patent No.: US 8,536,313 B2
(45) Date of Patent: Sep. 17, 2013

(54) MONOCLONAL ANTIBODY HAVING NEUTRALIZING ACTIVITY AGAINST MMP13

(75) Inventors: Shoichi Naito, Toyonaka (JP); Junji Onoda, Toyonaka (JP); Akira Yamauchi, Toyonaka (JP); Yoshito Numata, Toyonaka (JP); Junji Kishono, Toyonaka (JP)

(73) Assignee: Shionogi & Co., Ltd., Osaka (JP)

( * ) Notice: Subject to any disclaimer, the term of this patent is extended or adjusted under 35 U.S.C. 154(b) by 598 days.

(21) Appl. No.: 12/668,201

(22) PCT Filed: Jul. 8, 2008

(86) PCT No.: PCT/JP2008/062306
§ 371 (c)(1),
(2), (4) Date: Jan. 7, 2010

(87) PCT Pub. No.: WO2009/008414
PCT Pub. Date: Jan. 15, 2009

(65) Prior Publication Data
US 2010/0330092 A1 Dec. 30, 2010

(30) Foreign Application Priority Data

Jul. 10, 2007 (JP) .................. 2007-180784

(51) Int. Cl.
*C07K 16/40* (2006.01)
*C07K 16/00* (2006.01)
*A61K 39/395* (2006.01)

(52) U.S. Cl.
USPC ............... 530/388.26; 530/388.1; 530/387.9; 424/146.1; 424/141.1

(58) Field of Classification Search
None
See application file for complete search history.

(56) References Cited

FOREIGN PATENT DOCUMENTS

| WO | WO-98/29560 A1 | 7/1998 |
|---|---|---|
| WO | WO-2004/087042 A2 | 10/2004 |
| WO | WO-2007/065037 A2 | 6/2007 |

OTHER PUBLICATIONS

Engel et al. (Chem & Bio. 2005, 12:181-189).*
Merrell, M. A., et al., "Toll-Like Receptor 9 Agonists Promote Cellular Invasion by Increasing Matrix Metalloproteinase Activity," Mol Cancer Res, vol. 4, No. 7, pp. 437-447 (2006).
Mukhin, Y. V., et al., "Collagenase-2 and -3 Mediate Epidermal Growth Factor Receptor Transactivation by Bradykinin $B_2$ Receptor in Kidney Cells," J. Pharma. Exper. Therap., vol. 318, No. 3, pp. 1033-1043 (2006).
Peeters-Joris, C., et al., "Differential regulation of MMP-13 (collagenase-3) and MMP-3 (stromelysin-1) in mouse calvariae," Biochimica et Biophysica Acta, vol. 1405, pp. 14-28 (1998).
Maskos, K. et al., "Flexibility and variablility of TIMP binding: X-ray structure of the complex between collagenase-3/MMP-13 and TIMP-2, J", J. Mol. Biol., 2007, vol. 366, No. 4, pp. 1222-1231.
Leeman, M.F. et al., "The structure, regulation, and function of human matrix metalloproteinase-13", Crit. Rev. Biochem. Mol. Biol., 2002, vol. 37, No. 3, pp. 149-166.
Billinghurst, R. C. et al., "Enhanced Cleavage of Type II Collagen by Collagenases in Osteoarthritic Articular Cartilage", J. Clin. Invest., 1997, vol. 99, No. 7, pp. 1534-1545.
Freije, J.M.P. et al., "Molecular Cloning and Expression of Collagenase-3, a Novel Human Matrix Metalloproteinase Produced by Breast Carcinomas", Journal of Biological Chemistry, 1994, vol. 269, No. 24, pp. 16766-16773.

* cited by examiner

*Primary Examiner* — Sharon Wen
(74) *Attorney, Agent, or Firm* — Birch, Stewart, Kolasch & Birch, LLP.

(57) ABSTRACT

A neutralizing monoclonal antibody specifically reacting with MMP13, a method of neutralizing enzyme activity of MMP13 and an immunological measuring method each using the antibody, as well as a diagnostic agent and a pharmaceutical composition containing the antibody, are provided. Various antibodies to MMP13 have been hitherto obtained, but an antibody having neutralizing activity against MMP13 has not been obtained. The present inventors intensively studied, as a result, found out a neutralizing antibody having specificity for MMP13, resulting in completion of the present invention.

12 Claims, 4 Drawing Sheets

MONOCLONAL ANTIBODY HAVING NEUTRALIZING ACTIVITY AGAINST MMP13

This application is a National Stage of PCT International Application No. PCT/JP2008/062306 filed on Jul. 8, 2008, which claims priority under 35 U.S.C. §119(a) to Patent Application No. 2007-180784 filed in Japan on Jul. 10, 2007.

TECHNICAL FIELD

The present invention relates to a neutralizing monoclonal antibody to MMP13. More particularly, the present invention relates to a method of neutralizing enzyme activity of MMP13 and an immunological measuring method, each using a monoclonal antibody having neutralizing activity against MMP13, as well as a diagnostic agent and a pharmaceutical composition containing the antibody.

BACKGROUND ART

An extracellular matrix is composed of complicated components including collagen such as type IV collagen, and adhering glycoproteins such as proteoglycan, elastin, fibronectin, laminin, and heparan sulfate. A group of enzymes collectively named matrix metalloproteinase (hereinafter, abbreviated as MMP) having different substrate specificities are implicated in degradation of this extracellular matrix. Hitherto, as MMP, interstitial collagenase (MMP1), 72 kDa gelatinase (also referred to as type IV collagenase or gelatinase A: MMP2), stromelysin-1 (MMP3), matrilysin (MMP7), neutrophil collagenase (MMP8), 92 kDa gelatinase (also referred to as type IV collagenase or gelatinase B: MMP9), stromelysin-2 (MMP10), stromelysin-3 (MMP11), macrophage metalloelastase (MMP12), collagenase 3 (MMP13), membrane-type MMP (MT-MMP) and the like have been reported.

MMP13 which is one of the MMPs is called collagenase 3 as another name, and is much expressed in chondrocyte which is situated deep in an articular cartilage, cancer or the like. MMP13 is an extracellular matrix degrading enzyme specific for type I to type III collagen and gelatin. MMP13 has very high specificity for type II collagen which is a main extracellular matrix of cartilage, and plays an important role in a metabolism of a cartilage. Osteoarthritis is a disease of a joint accompanied with destruction of an extracellular matrix containing mainly type II collagen, and denaturation of a cartilage, and MMP13 is implicated in development of osteoarthritis through destruction of an extracellular group (see e.g. Non-patent Document 1). It is expected that, by inhibiting activity of MMP13, degradation of type II collagen which is a main extracellular matrix of cartilage is suppressed, and development of osteoarthritis is suppressed. Therefore, a neutralizing antibody of MMP13 is useful as a drug for searching, diagnosing or treating an inhibitor of a disease in which MMP13 is implicated.

MMP13 is composed of a propeptide domain, a catalytic domain, and a hemopexin clotting enzyme-like domain at a C-terminus, following a signal peptide at an N-terminus. In the catalytic domain, a zinc ion binding region to which a zinc ion essential for activity binds is present. An amino acid sequence of the catalytic domain is conserved throughout species, and the catalytic domain of human has 94%, 94%, 98%, and 96% homology to that of rat, mouse, dog and rabbit, respectively. In addition, the catalytic domain of human MMP13 has high homology to that of human MMP2, MMP1, MMP8, and MMP9, and has 77%, 73%, 73% and 73% homology thereto, respectively. There is a possibility that an antibody recognizing the catalytic domain of MMP13 has neutralizing activity, but the catalytic domain of MMP13 has high homology to the catalytic domain of human MMP2, MMP1, MMP8, and MMP9, and it is difficult to obtain a neutralizing antibody specifically recognizing MMP13.

As an antibody recognizing MMP13, there has hitherto been reported that a polyclonal antibody to recombinant MMP13 produced in *Escherichia coli* was made in a rabbit, in which the polyclonal antibody is used for staining a tissue of a breast cancer (see Non-patent Document 2). On the other hand, as a monoclonal antibody recognizing MMP13, a monoclonal antibody specifically reacting with both of active-type MMP13 and latent-type MMP13, a monoclonal antibody specifically reacting only with latent-type MMP13, or an antibody specifically reacting only with active-type MMP13 has been reported (see Patent Document 1). Those monoclonal antibodies do not cross-react with other matrix metal proteases, and can be used in a method of separating and quantitating latent-type MMP13 and active-type MMP13. However, there is not reported that these antibodies inhibit enzyme activity of MMP13.

Patent Document 2 describes an antibody which binds to MMP2 and MMP9, and inhibits enzyme activities thereof, and a monoclonal antibody is made using a hapten consisting of a metal ion and porphyrin, which is a structure common to a zinc ion binding region of MMP family. Therefore, this antibody has a problem in properties.

In the catalytic domain of MMP13, since the catalytic domain and the amino acid sequence of MMP2, MMP1, MMP8, MMP9 and the like are conserved as described above, it is difficult to make a neutralizing antibody which recognizes a region involved in activity of MMP13 and has MMP13-specific reactivity. Actually, there is not reported that a neutralizing monoclonal antibody inhibiting enzyme activity of MMP13 was obtained using MMP13 or a peptide thereof as an antigen.

Patent Document 1: International Publication WO 98/29560 pamphlet
Patent Document 2: International Publication WO 20000/087042 pamphlet
Non-patent Document 1: J. Clin. Invest., 1997, vol. 99, No. 7, pp. 1584-1545
Non-patent Document 2: J. Biol. Chem., 1994, vol. 269, pp. 16766-16773

DISCLOSURE OF THE INVENTION

Problems to be Solved by the Invention

A monoclonal antibody specifically reacting with MMP13, which is currently known, has no neutralizing activity. Therefore, a neutralizing antibody which can be used in searching an inhibitor of MMP13, analyzing the function of MMP13, diagnosing a disease in which MMP13 is implicated, or treating a disease in which MMP13 is implicated, is sought. An object of the present invention is to provide a neutralizing monoclonal antibody specifically reacting with MMP13, a method of neutralizing enzyme activity of MMP13 and an immunological measuring method each using the antibody, as well as a diagnostic agent and a pharmaceutical composition containing the antibody.

Means to Solve the Problems

Various antibodies to MMP13 have been hitherto obtained, but an antibody having neutralizing activity against MMP13 has not been obtained. The present inventors intensively studied, as a result, found out a neutralizing antibody having specificity for MMP13, resulting in completion of the present invention.

The present invention relate to:
(1) A monoclonal antibody that specifically binds to MMP13, wherein the antibody inhibits protease activity of MMP13;
(2) The monoclonal antibody according to (1), wherein the antibody binds to a polypeptide consisting of an amino acid sequence of SEQ ID NO: 1;
(3) The monoclonal antibody according to (1) or (2), wherein the antibody binds to a polypeptide consisting of an amino acid sequence of SEQ ID NO: 2;
(4) The monoclonal antibody according to any one of (1) to (3), wherein the antibody has a nature of a monoclonal antibody produced by a hybridoma having an accession number of FERM ABP-10968;
(5) The monoclonal antibody according to any one of (1) to (4), wherein the antibody is a monoclonal antibody produced by a hybridoma having an accession number of FERM ABP-10968;
(6) The monoclonal antibody according to any one of (1) to (4), wherein the antibody is a human antibody;
(7) A hybridoma producing the monoclonal antibody as defined in any one of (1) to (6);
(8) The hybridoma according to (7), wherein an accession number is FERM ABP-10968;
(9) An immunological assay method of MMP13, comprising the use of the monoclonal antibody as defined in any one of (1) to (6);
(10) A method of neutralizing enzyme activity of MMP13, including using the monoclonal antibody as defined in any one of (1) to (6);
(11) A diagnostic agent for a disease in which MMP13 is implicated, containing the monoclonal antibody as defined in any one of (1) to (6);
(12) The diagnostic agent according to (11), wherein the disease in which MMP13 is implicated is osteoarthritis;
(13) A pharmaceutical composition for treating or preventing a disease in which MMP13 is implicated, containing the monoclonal antibody as defined in any one of (1) to (6);
(14) The pharmaceutical composition according to (13), wherein the disease in which MMP13 is implicated is osteoarthritis;
(15) A method of treating or preventing a disease in which MMP13 is implicated, including a step of administering a pharmaceutical composition containing the monoclonal antibody as defined in any one of (1) to (6);
(16) The method of treating or preventing a disease according to (15), wherein the disease in which MMP13 is implicated is osteoarthritis;
(17) Use of the monoclonal antibody as defined in any one of (1) to (6) in production of a medicament for treating or preventing a disease in which MMP13 is implicated;
(18) The use for production of a medicament according to (17), wherein the disease in which MMP13 is implicated is osteoarthritis;
(19) The monoclonal antibody as defined in any one of (1) to (6), for use in treatment or prevention of a disease in which MMP13 is implicated; and
(20) The monoclonal antibody according to (19), wherein the disease in which MMP13 is implicated is osteoarthritis.

Effect of the Invention

According to the present invention, a monoclonal antibody which specifically reacts with MMP13 and neutralizes enzyme activity of MMP13 can be obtained and, by using the obtained monoclonal antibody, immunological measurement or function analysis of MMP13 can be performed. According to the present invention, a diagnostic agent or a pharmaceutical composition containing the monoclonal antibody can be further obtained. Particularly, MMP13 is reported to play an important role in cancer metastasis or arthritis such as rheumatism, and is useful in diagnosing or treating such a disease.

BEST MODE FOR CARRYING OUT THE INVENTION

Figure 1:
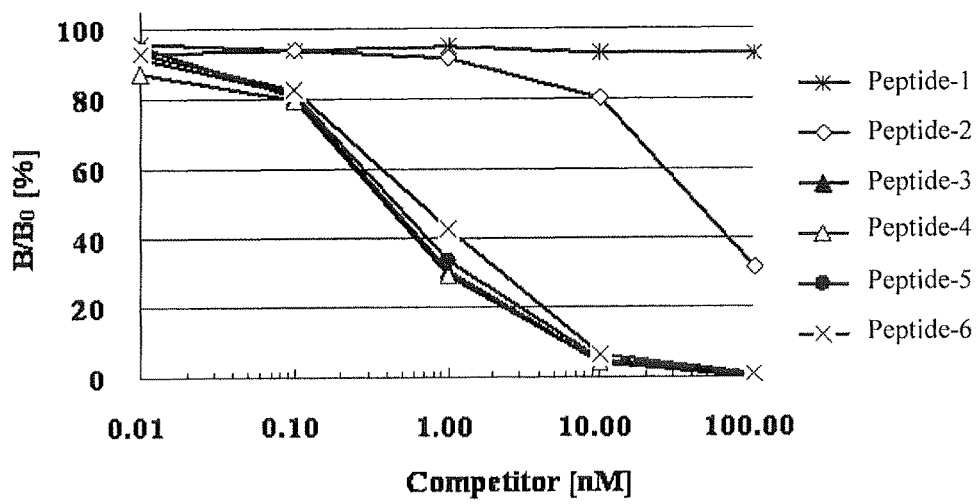
FIG. 1 shows a substitution curve by an MMP13 partial peptide (1-6) for binding of an MMP13 antibody (14D10) and an immunogenic peptide.

Terms used herein are used in a sense which is usually used in the art, unless otherwise is indicated.

The "MMP13" referred in the present invention means MMP13 of a mammal, particularly preferably means MMP13 derived from human. The mammal means human, cow, goat, rabbit, mouse, rat, hamster, and guinea pig, preferably human, rabbit, rat, hamster or mouse, and particularly preferably human, rat, or mouse. MMP13 derived from a human refers to a polypeptide consisting of an amino acid sequence represented by SEQ ID NO: 1. The amino acid sequence of rat MMP13 is described in GeneBank Accession Number; P23097. The amino acid sequence of mouse MMP13 is described in GeneBank Accession Number; P33435. The "MMP13" referred in the present invention includes an amino acid sequence of MMP13 of each mammal, particularly preferably a polypeptide having substantially the same amino acid sequence as the amino acid sequence of human MMP13.

Herein, the "polypeptide having substantially the same amino acid sequence" means the following mutant polypeptide. That is, it may be a mutant polypeptide having the amino acid sequence in which a plurality of amino acids, preferably 1 to 10 amino acids, and particularly preferably 1 to 5 amino acids are substituted, deleted and/or modified in the amino acid sequence, as well as a mutant polypeptide having an amino acid sequence in which a plurality of amino acids, preferably 1 to 10 amino acids, and particularly preferably 1 to 5 amino acids are added to an amino acid sequence of natural MMP13 (particularly preferably, human-derived MMP13) and, further, a mutant polypeptide having a plurality of such substitution, deletion, modification and addition, as far as it has substantially the equivalent biological nature to that of the natural MMP13 (particularly preferably, human-derived MMP13).

MMP13 in the present invention, particularly human MMP13 can be produced by appropriately using the methods known in the art such as a chemical synthesizing method, a cell culturing method and the like, or the modified methods, in addition to gene recombinant technique. Such substitution, deletion or insertion of an amino acid can be performed according to a normal method (for example, Experimental Medicine separate volume "Genetic Technology Handbook" (1992)).

The "protease activity of MMP13" in the present invention means matrix metalloproteinase activity possessed by MMP13. A region involved in protease activity of MMP13 is an arbitrary region on an amino acid sequence of MMP13, and means a region in which matrix metalloproteinase activity possessed by MMP13 is changed by binding of an antibody to the region. Preferably, it means a catalytic region, and particularly preferably means a zinc ion binding region. On an amino acid sequence of human MMP13 represented by SEQ ID NO: 1, the catalytic region is 104 position to 274 position, and the zinc ion binding region means a region of 222 position to 232 position.

The "neutralizing antibody" in the present invention means an antibody which can inhibit matrix metalloproteinase activity possessed by MMP13.

The "monoclonal antibody" of the present invention includes not only a monoclonal antibody derived from a non-human mammal, but also a human monoclonal antibody. Herein, the human monoclonal antibody includes a chimeric monoclonal antibody, a human-type monoclonal antibody, and a human monoclonal antibody. Since the human monoclonal antibody has reduced antigenecity in human body, it is useful as an active ingredient of a therapeutic agent of the present invention.

Herein, the "chimeric monoclonal antibody" is a monoclonal antibody made by genetic engineering and, more particularly, means a monoclonal antibody such as a mouse/human chimeric monoclonal antibody and the like, in which a variable region thereof is a variable region derived from immunoglobulin of a non-human mammal (mouse, rat, hamster, and the like), and a constant region thereof is a constant region derived from human immunoglobulin. The chimeric antibody is obtained by ligating a DNA encoding a variable region with a DNA encoding a human antibody constant region, incorporating it into an expression vector, and introducing the vector into a host, followed by production (see International Publication WO 96/02576).

In addition, the "human-type monoclonal antibody" means a monoclonal antibody made by genetic engineering, and more particularly, means a monoclonal antibody in which a part or all of a complementarity determining region of a supervariable region thereof is a complementarity determining region of a supervariable region derived from a monoclonal antibody of a non-human mammal (mouse, rat, hamster, and the like), a framework region of a variable region thereof is a framework region of a variable region derived from human immunoglobulin. A humanized antibody is obtained by transplanting a complementarity determining region (CDR) of a mammal other than a human, for example, a mouse antibody into a framework region of a human antibody (see International Publication WO 96/02576 pamphlet).

Herein, the "human monoclonal antibody" is a human monoclonal antibody which binds to the above-defined MMP13 or a part thereof. More particularly, it is human immunoglobulin in which all regions including a variable region of a heavy chain (H chain) and a constant region of the H chain as well as a variable region of a light chain (L chain) and a constant chain of the L chain constituting immunoglobulin are derived from a gene encoding human immunoglobulin.

The human monoclonal antibody can be produced by immunizing a human antibody-producing transgenic non-human mammal like a human antibody-producing transgenic mouse described later with any immunogen (antigen) of the aforementioned MMP13 or a peptide thereof according to the current general process for producing a monoclonal antibody.

The "transgenic human antibody-producing non-human mammal," particularly, human antibody-producing transgenic mouse which is a preferable embodiment herein can be made according to the previous report (Nature Genetics, Vol. 7, p. 13-21, 1994; Nature Genetics, Vol. 15, p. 146-156, 1997; JP-A No. 4-504365; JP-A No. 7-509137; Nikkei Science, June, p. 40-50, 1995; International Application Publication WO 94/25585; Nature, Vol. 368, p. 856-859, 1994; JP-A No. 6-500233; and the like).

The "immunological measuring method" of the present invention has principle of immunoassay. Specifically, principle of various methods described in enzyme immunoassay ($3^{rd}$ edition, edited by Eiji Ishikawa, et al., published by Igaku-Shoin Ltd., 1987) can be applied. Preferable examples of applicable principle include single antibody solid phase method, double antibody liquid phase method, double antibody solid phase method, sandwich method, and one pot method described in JP-A No. 2-39747. In addition, as assay utilizing an antigen antibody reaction, EMIT method (Enzyme multiplied immunoassay technique), Enzyme channeling immunoassay. Enzyme modulator mediated enzyme immunoassay (EMMIA), Enzyme inhibitor immunoassay, Immunoenzymometric assay, Enzyme enhanced immunoassay and Proximal linkage immunoassay are also known.

Any principle of such the immunoassays can be used by appropriate selection depending on the purpose, but in view of operational simplicity and/or economical utility, particularly clinical general-use, it is preferable to use principle of a sandwich method, a one pot method, or a single antibody solid phase method, more preferably principle of a sandwich method or a one pot method. Particularly preferable is a sandwich method using a multi-well microtiter plate having many wells, a representative of which is a 96-well microplate, or a one pot method using beads in which a polypeptide is immobilized on a surface thereof, and a labeled counterpart labeled with an enzyme such as peroxidase, or biotin.

As a sample which is measured by the "immunological measuring method" of the present invention, a body fluid such as plasma, serum, urine, joint fluid, a cell culturing solution, and a tissue culturing solution can be used. These samples can be a sample for a method of immunoassay, as it is, or by diluting or extracting with various buffers followed by concentration. As a solvent used in dilution or extraction of a sample, any buffer or organic solvent may be used, preferably a buffer for immunoassay, water, physiological saline, an acetate buffer, acetone, chloroform-methanol, or these solutions containing a surfactant can be used. The "immunological assay method of MMP13" of the present invention provides an excellent method of separating and quantitating MMP13 in a test sample using a monoclonal antibody to MMP13, and a monoclonal antibody to MMP13 as a solid carrier, and a reagent kit therefor. Preferably, it is useful as a diagnostic agent of a disease in which MMP13 is implicated. Particularly preferably, it is useful as a diagnostic agent which can diagnose cancer, rheumatism, or osteoarthritis.

The "method of neutralizing enzyme activity of MMP13" of the present invention means a method of inhibiting enzyme activity of MMP13 using an MMP13 monoclonal antibody for the purpose of analyzing physiological function of MMP13 and searching the function of an MMP13 inhibitor. For example, an MMP13 monoclonal antibody is added to chondrocytes in advance. Then, by adding IL-1, chondrocytes are stimulated, and expression of MMP13 is induced. When degradation of an extracellular matrix is suppressed by addition of the antibody, it can be shown that mainly MMP13 is responsible for degradation of an extracellular matrix in chondrocytes.

The "disease in which MMP13 is implicated" in the present invention is not particularly limited as far as it is a disease in which MMP13 is implicated, and examples thereof include cancer, rheumatism, and osteoarthritis. Particularly, since in osteoarthritis, by inhibiting activity of MMP13, degradation of an extracellular matrix of cartilage is suppressed, and its development is suppressed, application of the present invention is expected.

The pharmaceutical composition of the present invention can be parenterally administered systemically or locally. For example, intravenous injection such as infusion, intravascular injection, intraperitoneal injection, and subcutaneous injection can be selected, and an administration method can be appropriately selected depending on an age and symptom of a patient. The pharmaceutical composition of the present invention may contain a pharmaceutically acceptable carrier and an additive depending on an administration route.

Examples of such a carrier and additive include water, pharmaceutically acceptable organic solvent, collagen, polyvinyl alcohol, polyvinylpyrrolidone, carboxyvinyl polymer, carboxymethylcellulose sodium, poly(sodium acrylate), sodium alginate, water-soluble dextran, carboxymethyl starch sodium, pectin, methyl cellulose, ethyl cellulose, xanthan gum, gum arabic, casein, gelatin, agar, diglycerin, propylene glycol, polyethylene glycol, vaseline, paraffin, stearyl alcohol, stearic acid, human serum albumin (HSA), mannitol, sorbitol, lactose, and a surfactant which is acceptable as a pharmaceutical additive. An additive to be used is selected appropriately or in combination from the aforementioned additives depending on a dosage form, being not limited thereto.

The pharmaceutical composition comprising a human antibody of the present invention is useful as a medicament for inhibiting, or arresting development and/or progression of a disease in which MMP13 is implicated, or treating or preventing the disease.

EXAMPLES

The present invention will be specifically explained by way of Examples, but the present invention is not limited to the following Examples. As an antibody making procedure, a method described in Immunochemistry in Practice (Blackwell Scientific Publications) was used, unless otherwise is indicated. In addition, as a gene manipulation procedure, a method described in Molecular Cloning: A Laboratory Manual, $2^{nd}$ Edition (Cold Spring Harbor Laboratory) was used, unless otherwise is indicated.

Example 1

Selection of Antigen

In order that an antibody inhibits enzyme activity of MMP13, although the antibody is desirably an antibody recognizing the catalytic center of MMP-13, the catalytic center of MMP13 is embedded in the interior of the protein. For this reason, it is predicted that it is difficult for an antibody to bind the catalytic center. Then, the region of MMP-13 which is both close to the catalytic center of MMP13 and exposed on the surface of the MMP-13 is desirable. Then, referring to a steric structure of the catalytic domain of human MMP13 (Protein Data Bank ID: 1YOU), a partial peptide consisting of an amino acid sequence of 225 position to 246 position of human MMP13 described in SEQ ID NO: 2 was selected as an immunogen. In addition, since an amino acid sequence of the selected partial peptide of MMP13 is a sequence common to human, mouse, rat, rabbit and dog, it is predicted that an antibody made by using the present peptide as an immunogen recognizes MMP13 derived from the a forementioned animal species.

Immunization of Antigen

A peptide (24 amino acids) in which glycine-cysteine was introduced into a C-terminus of the human MMP13 partial peptide (225-246) was synthesized (manufactured by Greiner Bio-one). Ten milligram of a synthetic human MMP13 partial peptide dissolved in 1 ml of 0.1 M phosphate buffer (pH 6.0) containing 5 mM EDTA, and 10 mg hemocyanine of giant keyhole limpets (maleimidated KLH, manufactured by PIERCE) dissolved in 1 ml of a 0.1 M phosphate buffer (pH 6.0) containing 5 mM EDTA containing 50% DMSO were mixed, and they were reacted at room temperature for 4 hours and, further, at 4° C. overnight. The mixed solution was dialyzed against distilled water, and lyophilized to obtain 11.53 mg of an MMP13 partial peptide-KLH complex. This was used as an immunogen. One hundred microgram of the prepared MMP13 partial peptide-KLH complex and Freund's complete adjuvant were intraperitoneally administered to seven A/J Jms Slc male mice (4 weeks old), this was used as priming. Thereafter, after 21 days and 42 days, 100 μg of the MMP13 partial peptide-KLH complex and Freund's incomplete adjuvant were administered, and this was used as booster immunization. Further, after 71 days, a solution obtained by suspending 100 μg of the human MMP13 partial peptide-KLH complex in 0.1 ml of a physiological saline was intraperitoneally administered, and this was used as final immunization.

Biotin Labeling of Human MMP13 Partial Peptide

The synthetic human MMP13 partial peptide (0.4 mg) dissolved in 0.4 ml of 0.1 M phosphate buffer (pH 6.0) containing 5 mM EDTA, and 160 μg of PEO-Maleimide activated biotin (manufactured by PIERCE) dissolved in 80 μl of distilled water were mixed, this was reacted at room temperature for 2 hours and, thereafter, biotin-labeled human MMP13 partial peptide was purified by reverse phase HPLC.

Preparation of Hybridoma

Three days after final immunization, spleen was isolated, and splenocyte was recovered. The splenocyte and mouse myeloma cell (p3×63-Ag8.U1, manufactured by Tokyo Shuryu Research Institute) were fused using 50% polyethylene glycol 4000, and the fused cell was selected on a medium containing hypoxanthine, aminopterin and thymidine.

Preparation of Recombinant rat MMP13 Catalytic Domain

A DNA fragment encoding the catalytic domain (amino acids: 99-262) of rat MMP13 was inserted into an expression vector pTrc99AHE via restriction enzyme sites Bst1107 and XbaI, and this was transformed into *Escherichia coli* (XL-1Blue) according to a conventional method to obtain recombinant *Escherichia coli* (MMP13-XL-1 Blue). The MMP13-XL-1 Blue was cultured in 200 ml of a LB/Ampicillin liquid medium at 37° C. and, when OD600 became 0.5, 200 μl of 0.1 M IPTG was added to induce expression of the rat MMP13 catalytic domain. Further, after culturing at 37° C. for 2 hours, fungal forms were centrifuged, and the insoluble fraction after ultrasound treatment was solubilized with 1 ml of an 8 M urea solution. Further, 1 ml of a buffer U (50 mM Tris buffer containing 6 M urea, 0.01 M $CaCl_2$, 0.3 M NaCl, and 0.005% Brij35, pH 7.9) was added, and this was centrifuged. The supernatant after centrifugation was purified using Ni-NTA agarose (manufactured by Quiagen). A solution containing the rat MMP13 catalytic domain was passed through the Ni-NTA agarose, and washed and eluted with a buffer U containing 20 mM imidazole. Refolding of the rat MMP13 catalytic domain in the eluted solution was performed by the following procedure. 2-Mercaptoethanol (7.8 µl) (manufactured by Nacalai tesque) was added per 1 ml of the eluted fraction, 19 ml of a buffer T (50 mM Tris buffer containing 0.01 M $CaCl_2$, 0.3 M NaCl, and 0.005% Brij35, pH 7.4) was gradually added while stirring and, thereafter, this was allowed to stand at 4° C. for 16 hours, and the supernatant after centrifugation was recovered.

Selection of MMP13 Antibody

Ten days after cell fusion, screening of a specific antibody-producing cell was performed. ELISA used in screening is as follows. A Tris buffer (35 µl) (50 mM Tris-HCl, pH 7.5) containing 0.35 µg of an anti-mouse IgG antibody (manufactured by Shibayagi Co., Ltd.) was added to each well of a 384-well microtiter plate (manufactured by Nunc), and the antibody was immobilized at 4° C. for 16 hours. After these wells were washed with 90 µl of a washing solution (physiological saline containing 0.01% Tween 20) once, 200 µl of BlockAce (manufactured by Dainippon Pharma Co., Ltd.) was added, this was allowed to stand at room temperature for 2 hours, and blocking was performed (anti-mouse IgG antibody-solid phased plate). After each well was washed with 90 µl of a washing solution once, 10 µl of a buffer A (50 mM Tris buffer containing 0.5% bovine serum albumin, 0.01% Tween 80, 0.05% Proclin 150, and 0.15 M NaCl, pH 7.4) containing 15 µl of the hybridoma culturing supernatant and 30 nM recombinant rat MMP13 catalytic domain, and 10 µl of a buffer A containing 0.05 ng of biotin-labeled human MMP13 partial peptide and 2 ng of Streptavidin-HRP (manufactured by PIERCE) were added to react them at 4° C. for 16 hours. Then, after each well was washed with 90 µl of a washing solution three times, 25 µl of TMB+-Substrate-Chromogen (manufactured by DAKO) was added to develop a color at room temperature for 30 minutes, 25 µl of 0.05 M sulfuric acid was added to stop a reaction, and an absorbance at 450 nm was measured. From results of screening, 7 clones of a hybridoma exhibiting strong affinity for the rat recombinant MMP13 catalytic domain were selected, and they were cloned two times by a limiting dilution method to obtain clones of a hybridoma producing a monoclonal antibody which recognizes MMP13. Regarding obtained 7 clones, two clones having high specificity for MMP13 were selected and, among the two clones, one clone inhibiting enzymatic activity of MMP-13 strongly was selected, and was named 14D10. Regarding 14D10, a subclass of an antibody was determined using a mouse monoclonal antibody isotyping ELISA kit (manufactured by BD Bioscience) and, as a result, an isotype of 14D10 was IgG2a.

A hybridoma producing the monoclonal antibody 14D10 of the invention has been deposited in Advanced Industrial Science and Technology, International Patent Organism Depositary (Ibaragi-ken, Tsukuba-shi, Higashi 1-1-1 Central 6) on May 21, 2008 as an accession number of FERM BP 10968.

Example 2

Identification of Epitope Recognized by MMP-13 Antibody (14D10)

In order to identify an epitope of the MMP13 antibody (14D10), a human MMP13 partial peptide was synthesized with Peptide Synthesizer Model 431A (manufactured by Applied Biosystems). The synthesized peptides are six kinds of peptide-1 (amino acid sequence of 239 position to 246 position of human MMP13), peptide-2 (amino acid sequence of 234 position to 246 position of human MMP13), peptide-3 (amino acid sequence of 231 position to 246 position of human MMP13), peptide-4 (amino acid sequence of 229 position to 246 position of human MMP13), peptide-5 (amino acid sequence of 227 position to 246 position of human MMP13), and peptide-6 (amino acid sequence of 225 position to 246 position of human MMP13). ELISA for determining the antigen recognizing site was performed by the following method. A Tris buffer (50 mM Tris-HCl, pH 7.5) (150 µl) containing 1.5 µg of an anti-mouse IgG antibody (manufactured by Shibayagi) was added to a 96-well microtiter plate (manufactured by NUNC), followed by immobilization at 4° C. for 16 hours. These wells were washed with 300 µl of a washing solution (physiological saline containing 0.01% Tween 20), 300 µl of BlockAce (manufactured by Dainippon Pharma Co., ltd.) was added, this was allowed to stand at room temperature for 2 hours, and blocking was performed (anti-mouse IgG antibody-solid phased plate). After each well was washed with 300 µl of a washing solution, 50 µl of a buffer A containing 100 nM various MMP13 partial peptides (1-6), and 50 µl of a buffer A containing 0.1 ng of a biotin-labeled human MMP13 partial peptide (225-246) and 4 ng of Streptavidin-HRP (manufactured by PIERCE), and 50 µl of a buffer A containing 0.5 ng of an MMP13 antibody (14D10) were added to react them at room temperature for 3 hours. Then, after each well was washed with 300 µl of a washing solution three times, 100 µl of TMB+-Substrate-Chromogen (DAKO) was added to develop a color at room temperature for 30 minutes, 100 µl of 0.05 M sulfuric acid was added to stop a reaction, and an absorbance at 450 nm was measured. As a result, since binding of an MMP13 antibody and a biotin-labeled human MMP13 partial peptide (225-246) was slightly inhibited with peptide-2, and was completely inhibited with peptide-3, it was shown that an antigen recognizing site of the MMP13 antibody (14D10) was a peptide comprising an amino acid sequence of 231 position to 233 position of human MMP13 (FIG. 1).

Example 3

Confirmation of MMP13 Specificity by ELISA

Figure 2:
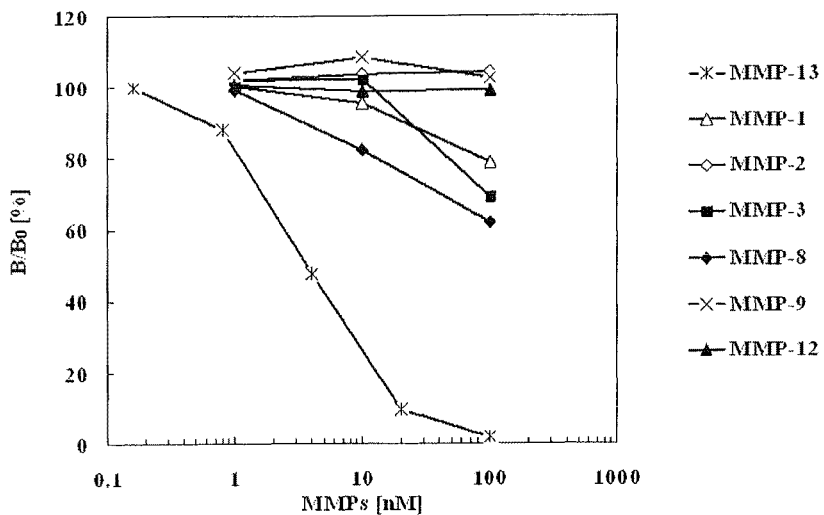
FIG. 2 shows a substitution curve by an MMP family for binding of an MMP13 antibody (14D10) and an immunogenic peptide.
Figure 3:
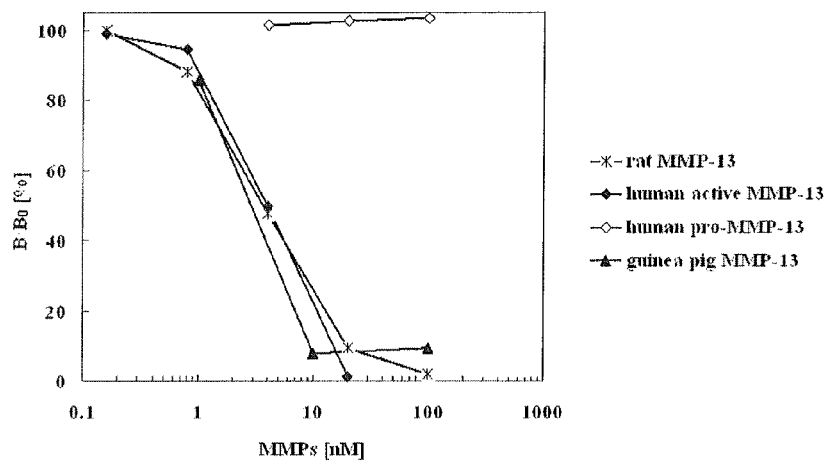
FIG. 3 shows a substitution curve by a rat MMP13 catalytic domain, a guinea pig MMP13 catalytic domain, or human MMP13 (active-type, precursor-type).

ELISA for investigating specificity of the MMP13 antibody (14D10) was performed by the following method. A Tris buffer (50 mM Tris-HCl, pH 7.5) (150 µl) containing 1.5 µg of an anti-mouse IgG antibody (manufactured by Shibayagi) was added to a 96-well microtiter plate (manufactured by Nunc), followed by immobilization at 4° C. for 16 hours. These wells were washed with 300 µl of a washing solution (physiological saline containing 0.01% Tween 20), 300 µl of BlockAce (manufactured by Dainippon Pharma Co. Ltd.) was added, this was allowed to stand at room temperature for 2 hours, and blocking was performed (anti-mouse IgG antibody-solid phased plate). Each well was washed with 300 µl of a washing solution once, 50 µl of a buffer A containing 100, 10 or 1 nM each human MMP catalytic domain (MMP-1, MMP-2, MMP-3, MMP-8, MMP-9), 100, 20, 4, 0.8 or 0.16 nM rat MMP13 catalytic domain, a guinea pig MMP13 catalytic domain, 100, 10 or 1 nM human Pro-MMP13 (manufactured by R&D SYSTEMS), or 20, 4, 0.8 or 0.16 nM human Active-MMP13 (Pro-MMP13 was activated with APMA according to instructions of product), 50 µl of a buffer A containing 0.1 ng of a biotin-labeled human MMP13 partial peptide (225-246) and 4 ng of Streptavidin-HRP (manufactured by PIERCE), and 50 µl of a buffer A containing 0.5 ng of an MMP13 antibody (14D10) were added to react them at 4° C. for 16 hours. Then, after each well was washed with 300 µl of a washing solution three times, 100 µl of TMB+-Substrate-Chromogen (DAKO) was added to develop a color at room temperature for 30 minutes, 100 µl of 0.05 M sulfuric acid was added to stop a reaction, and an absorbance at 450 nm was measured. As a result, it was found that the MMP13 antibody (14D10) reacted with human, rat or guinea pig MMP13, specifically, and did not react other MMPs (FIG. 2), and reacted with active-type MMP13, and did not react with precursor-type MMP13 (FIG. 3). In addition, it was found that it also reacted with guinea pig MMP13 having a different amino acid sequence from that of a peptide of an immunogen, and it was indicated that the present MMP13 antibody (14D10) recognized active-type MMP13 derived from extensive animal species.

Example 4

Figure 4:
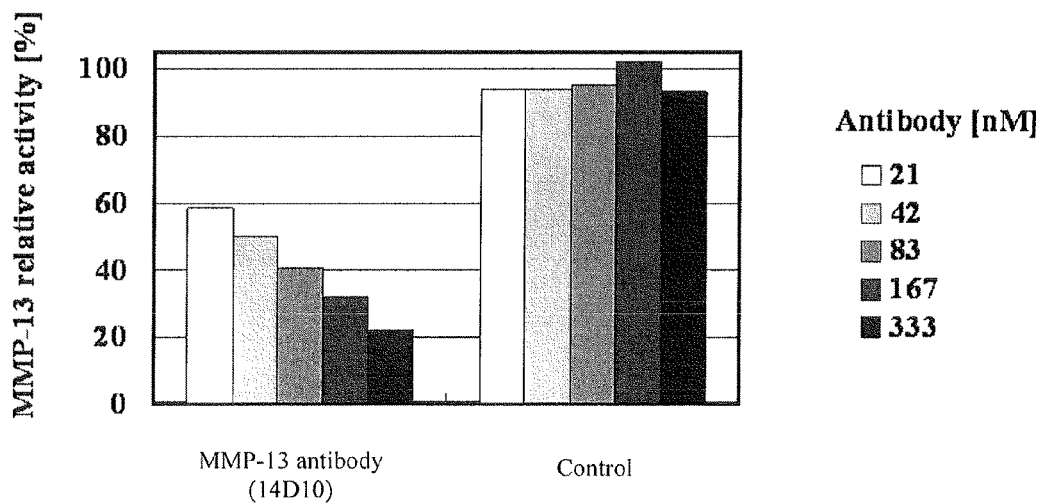
FIG. 4 shows inhibition of MMP13 enzyme activity with an MMP13 antibody using a synthetic substrate.

MMP13 Enzyme Activity Inhibiting Test with MMP13 Antibody Using Peptide Substrate To 384 low volume plate (manufactured by Corning) was added 10 µL of a rat MMP13 catalytic domain diluted with an MMP activity measuring buffer (50 mM Tris buffer containing 0.3 M NaCl, 10 mM $CaCl_2$, and 0.005% Brij35, pH 7.6), and 5 µL of an MMP activity measuring buffer containing an MMP13 antibody (14D10) was added. After allowing to stand at room temperature for 1 hour, 5 µL of an MMP activity measuring buffer containing 130 nM MMP peptide substrate (manufactured by Peptide Institute Inc.) was added. After allowing to stand at room temperature for 1 hour, a fluorescent signal (ex. 340 nm, em. 405 nm) was measured using EnVision (manufactured by PerkinElmer, Inc.). As a result, the peptide substrate cutting activity of MMP13 was inhibited with the MMP13 antibody (14D10) (FIG. 4).

Example 5

Figure 5:
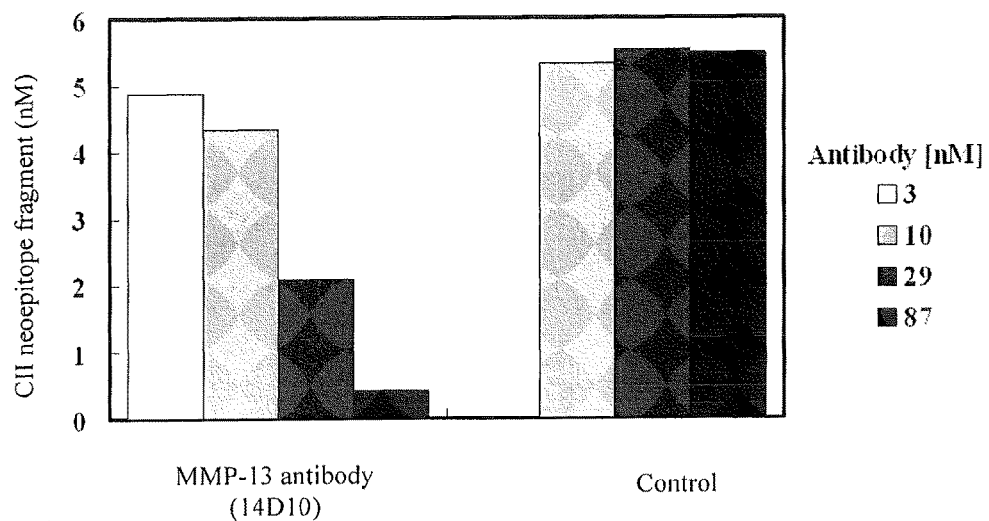
FIG. 5 shows inhibition of MMP13 enzyme activity with an MMP13 antibody using type II collagen.

MMP13 Enzyme Activity Inhibiting Test with MMP13 Antibody Using II Type Collagen Five ng/ml of human II type collagen solution (manufactured by Chondrex) was added to 96-well Maxisorp plate (manufactured by Nunc) and was incubated at 4° C. overnight, washed with a washing buffer (50 mM Tris buffer, pH 7.6) twice, and was used as a coating plate. To an enzyme reaction buffer (50 mM Tris buffer containing 0.3 M NaCl, 10 mM $CaCl_2$, and 0.005% Brij35, pH 7.6) were added human recombinant MMP13 (human Pro-MMP13 (manufactured by Calbiochem) was incubated with APMA (1 mM) at 37° C. for 2 hours to convert into active-type) and the MMP13 antibody (14D10), this was pre-incubated at room temperature for 2 hours, and then an enzyme reaction solution was added to the coating plate to initiate a reaction. After reacted at 37° C. for 4 hours, a stopping solution (EDTA, final concentration 5 mM) was added to stop an enzyme reaction, and the reaction solution was recovered. CII neoepitope (II type collagen degradation product) contained in the reaction solution was quantitated by ELISA with an antibody made by the same method as that of Reference Publication. As a result, the II type collagen cutting activity of MMP13 was inhibited with the MMP13 antibody (14D10) (FIG. 5).

Example 6

Figure 6:
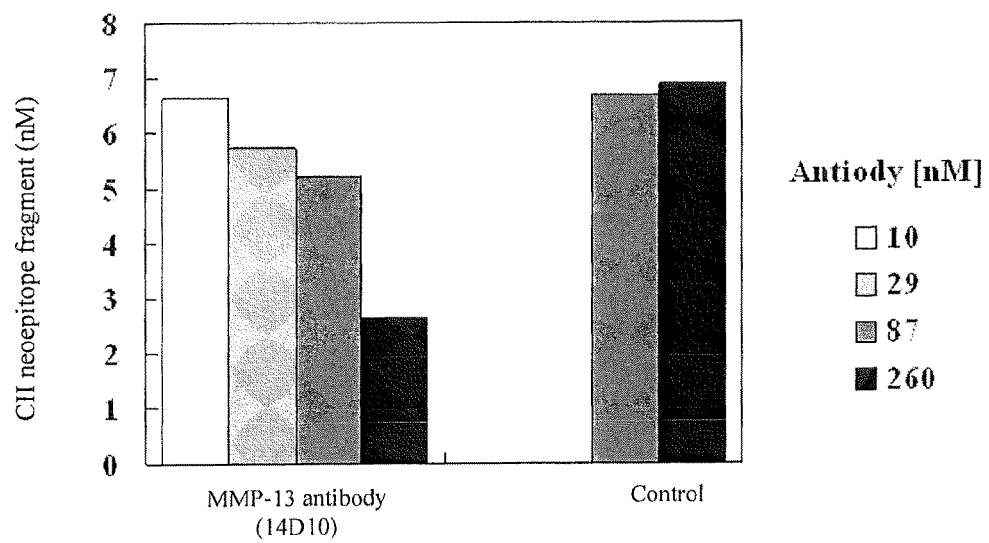
FIG. 6 shows the inhibiting effect of an MMP13 antibody (14D10) in a method of assessing collagen degradation inhibiting activity by MMP13 using a human cartilage monolayer culturing system.

MMP13 Enzyme Activity Inhibiting Test with MMP13 Antibody in Human Chondrocyte Culturing System Ten ng/ml of a human II type collagen solution (manufactured by Chondrex) was added to 96-well culturing plate (manufactured by Sumitomo Bakelite Co., Ltd.) and was incubated at 4° C. overnight, and washed with a culturing medium (DMEM containing 0.1 mg/ml BSA, ITS, and 50 µM L(+)-Ascorbic acid) once, and this was used as a coating plate. The normal human-derived chondrocytes (Cambrex) were seeded on the coating plate at $4 \times 10^4$ cells/well, and were cultured at 37° C. in 5% $CO_2$ using a culturing medium. After one day, the culturing solution was exchanged, the MMP13 antibody (14D10) was added, and 1 ng/ml human IL-1beta and 10 ng/ml Oncostatin M (manufactured by Sigma) were added, followed by culturing. After four days, a reaction stopping solution (EDTA, final concentration 5 mM) was added, and the culturing supernatant was recovered. CII neoepitope (II type collagen degradation product) contained in the culturing supernatant was quantitated by ELISA with an antibody made according to the same method as that of Reference Publication (Osteoarthritis and Cartilage, 2003, vol. 11, No. 9, pp. 673-680). The II type collagen degrading activity with MMP produced and released from chondrocyte was inhibited with the MMP13 antibody (14D10) (FIG. 6).

Example 7

Immunological Measurement of MMP13

Figure 7:
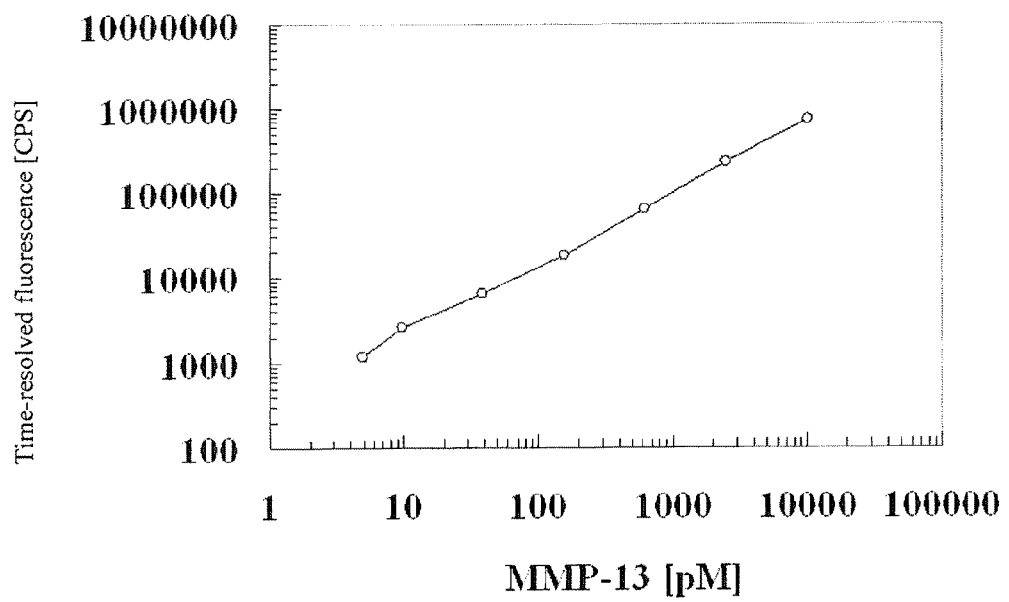
FIG. 7 shows a calibration line of an immunological assay method of MMP13 using an MMP13 antibody (14D10).

150 µl of a DELFIA Assay Buffer (manufactured by Perkin Elmer) containing 1.5 µg of the MMP13 antibody (14D10) was added to 96-well Maxisorp plate (manufactured by Nunc), followed by immobilization at 4° C. for 16 hours. These wells were washed with 300 µl of a washing solution (physiological saline containing 0.01% Tween 20) once, 300 µl of BlockAce (manufactured by Dainippon Pharma Co. Ltd.) was added, and this was allowed to stand at room temperature for 2 hours to perform blocking. Each well was washed with 300 µl of a washing solution once, human active MMP13 (human Pro-MMP13 (manufactured by R&D) activated with APMA according to instructions of product) was diluted into a buffer C containing 5 mM EDTA, and 150 µl of it was added. These were reacted at room temperature for 2 hours. Then, each well was washed with 300 µl of a washing solution three times, the MMP13 antibody (manufactured by Daiich Fine Chemical Co., Ltd.) which had been biotin-labeled with NHS-PEO4-Biotin (manufactured by PIERCE), and 150 µl of Streptavidin-Eu3+ (manufactured by PerkinElmer) were added to react them at 4° C. for 16 hours. Then, each well was washed with 300 µl of a washing solution three times, 150 µl of DELFIA Enhancement Solution (manufactured by PerkinElmer) was added, and time-resolved fluorescence was measured. As a result, a detection sensitivity of the active-type human MMP13 was 5 pM (FIG. 7).

Example 8

Comparison with Commercially Available Antibody in MMP13 Enzyme Activity Inhibiting Test Using Synthetic Substrate To 384 low volume plate (manufactured by Corning), 10 µL of a rat MMP13 catalytic domain diluted with an MMP activity measuring buffer (50 mM Tris buffer containing 0.3

Figure 8:
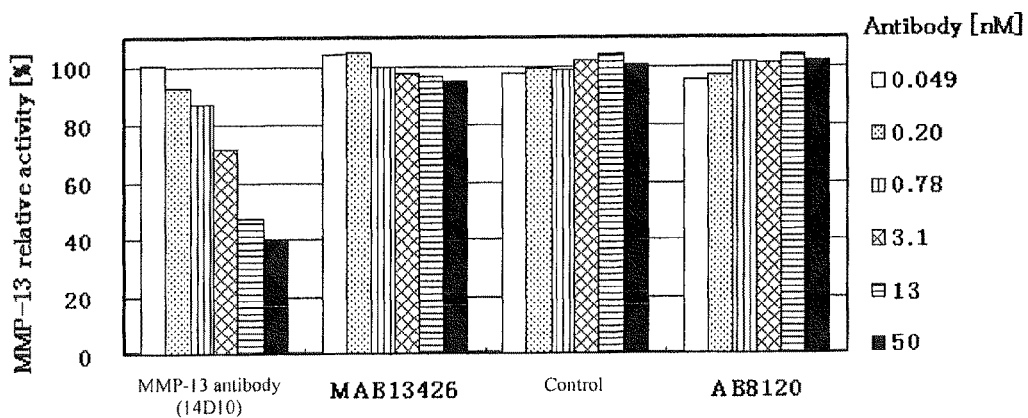
FIG. 8 shows inhibition of MMP13 enzyme activity with an MMP-13 antibody (14D10) or a commercially available MMP13 antibody using a synthetic substrate.

M NaCl, 10 mM CaCl$_2$, and 0.005% Brij35, pH 7.6) was added, and 5 μL of an MMP activity measuring buffer containing the MMP13 antibody (14D10), a commercially available MMP13 monoclonal antibody (manufactured by CHEMICON, catalog No.: MAB13426) or an MMP13 polyclonal antibody (manufactured by CHEMICON, catalog No.: AB8120) was added. After allowing to stand at room temperature for 1 hour, 5 μL of an MMP activity measuring buffer containing 130 nM MMP peptide substrate (manufactured by Peptide Institute) was added. After allowing to stand at room temperature for 1 hour, a fluorescent signal (ex. 340 nm, em. 405 nm) was measured using EnVision (manufactured by PerkinElmer, Inc.). As a result, the peptide substrate cutting activity of MMP13 was inhibited by the MMP13 antibody (14D10) (FIG. 8). However, the commercially available MMP13 monoclonal antibody (manufactured by CHEMICON, catalog No.: MAB13426) or the MMP13 polyclonal antibody (manufactured by CHEMICON, catalog No.: AB8120) did not inhibit the peptide substrate cutting activity of MMP13 (FIG. 8).

Industrial Applicability

In the present invention, a monoclonal antibody specifically reacting with MMP13 and neutralizing enzyme activity of MMP13 can be obtained and, by using the obtained monoclonal antibody, neutralization of enzyme activity of MMP13 and immunological measurement can be performed. Particularly, MMP13 is reported to play an important role in osteoarthritis, and the monoclonal antibody is useful as a diagnostic agent of a disease in which MMP13 is implicated, such as osteoarthritis. Further, according to the present invention, utilizing the fact that the monoclonal antibody has MMP13 neutralizing activity, a pharmaceutical composition containing the monoclonal antibody can be obtained. This pharmaceutical composition is useful as a therapeutic agent of a disease in which MMP13 is implicated, such as osteoarthritis.

Sequence Free Text

SEQ ID NO: 1 of Sequence Listing is a polypeptide of human MMP13.

SEQ ID NO: 2 of Sequence Listing is a partial peptide consisting of an amino acid sequence of 225 position~246 position of human MMP13.

The invention claimed is:

1. A monoclonal antibody that specifically binds to MMP13 protein and a polypeptide consisting of an amino acid sequence of SEQ ID NO: 2, wherein the antibody inhibits protease activity of MMP13 protein.

2. The monoclonal antibody according to claim 1, wherein the antibody is a monoclonal antibody produced by a hybridoma having an accession number of FERM BP-10968.

3. The monoclonal antibody according to claim 1, wherein the antibody is a human antibody.

4. A hybridoma producing the monoclonal antibody as defined in claim 1.

5. The hybridoma according to claim 4, wherein an accession number is FERM BP-10968.

6. An immunological assay method to detect or quantitate MMP13 protein, comprising a step of contacting the monoclonal antibody of claim 1 with MMP13 protein.

7. A diagnostic agent for a disease in which MMP13 is implicated, comprising the monoclonal antibody as defined in claim 1.

8. The diagnostic agent according to claim 7, wherein the disease in which MMP13 is implicated is osteoarthritis.

9. A pharmaceutical composition for treating or preventing a disease in which MMP13 is implicated, comprising the monoclonal antibody as defined in claim 1.

10. The pharmaceutical composition according to claim 9, wherein the disease in which MMP13 is implicated is osteoarthritis.

11. The monoclonal antibody according to claim 1 that is a humanized antibody.

12. The pharmaceutical composition according to claim 9, in which the monoclonal antibody is a humanized antibody.

* * * * *

UNITED STATES PATENT AND TRADEMARK OFFICE
CERTIFICATE OF CORRECTION

PATENT NO. : 8,536,313 B2
APPLICATION NO. : 12/668201
DATED : September 17, 2013
INVENTOR(S) : Shoichi Naito et al.

Page 1 of 1

It is certified that error appears in the above-identified patent and that said Letters Patent is hereby corrected as shown below:

ON THE TITLE PAGE:

At item (75), Inventors, change "Junji Kishono, Toyonaka (JP)" to --Junji Kishino, Toyonaka (JP)--.

Signed and Sealed this
Tenth Day of December, 2013

Margaret A. Focarino
*Commissioner for Patents of the United States Patent and Trademark Office*

SEQUENCE LISTING

```
<160> NUMBER OF SEQ ID NOS: 2

<210> SEQ ID NO 1
<211> LENGTH: 471
<212> TYPE: PRT
<213> ORGANISM: Homo sapiens

<400> SEQUENCE: 1

Met His Pro Gly Val Leu Ala Ala Phe Leu Phe Leu Ser Trp Thr His
1               5                   10                  15

Cys Arg Ala Leu Pro Leu Pro Ser Gly Gly Asp Glu Asp Asp Leu Ser
            20                  25                  30

Glu Glu Asp Leu Gln Phe Ala Glu Arg Tyr Leu Arg Ser Tyr Tyr His
        35                  40                  45

Pro Thr Asn Leu Ala Gly Ile Leu Lys Glu Asn Ala Ala Ser Ser Met
    50                  55                  60

Thr Glu Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95

Gly Val Pro Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
        115                 120                 125

Met Thr His Ser Glu Val Glu Lys Ala Phe Lys Lys Ala Phe Lys Val
    130                 135                 140

Trp Ser Asp Val Thr Pro Leu Asn Phe Thr Arg Leu His Asp Gly Ile
145                 150                 155                 160

Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Asp Glu Thr Trp Thr
        195                 200                 205

Ser Ser Ser Lys Gly Tyr Asn Leu Phe Leu Val Ala Ala His Glu Phe
    210                 215                 220
```

```
Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
            260                 265                 270

Pro Asn Pro Lys His Pro Lys Thr Pro Asp Lys Cys Asp Pro Ser Leu
        275                 280                 285

Ser Leu Asp Ala Ile Thr Ser Leu Arg Gly Glu Thr Met Ile Phe Lys
    290                 295                 300

Asp Arg Phe Phe Trp Arg Leu His Pro Gln Gln Val Asp Ala Glu Leu
305                 310                 315                 320

Phe Leu Thr Lys Ser Phe Trp Pro Glu Leu Pro Asn Arg Ile Asp Ala
                325                 330                 335

Ala Tyr Glu His Pro Ser His Asp Leu Ile Phe Ile Phe Arg Gly Arg
                340                 345                 350

Lys Phe Trp Ala Leu Asn Gly Tyr Asp Ile Leu Glu Gly Tyr Pro Lys
                355                 360                 365

Lys Ile Ser Glu Leu Gly Leu Pro Lys Glu Val Lys Lys Ile Ser Ala
                370                 375                 380

Ala Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
                405                 410                 415

Pro Arg Leu Ile Glu Glu Asp Phe Pro Gly Ile Gly Asp Lys Val Asp
                420                 425                 430

Ala Val Tyr Glu Lys Asn Gly Tyr Ile Tyr Phe Phe Asn Gly Pro Ile
                435                 440                 445

Gln Phe Glu Tyr Ser Ile Trp Ser Asn Arg Ile Val Arg Val Met Pro
450                 455                 460

Ala Asn Ser Ile Leu Trp Cys
465                 470

<210> SEQ ID NO 2
<211> LENGTH: 22
<212> TYPE: PRT
<213> ORGANISM: Homo sapiens

<400> SEQUENCE: 2

Gly His Ser Leu Gly Leu Asp His Ser Lys Asp Pro Gly Ala Leu Met
1               5                   10                  15

Phe Pro Ile Tyr Thr Tyr
                20
```